United States Patent [19]

Karos

[11] Patent Number: 4,497,402

[45] Date of Patent: Feb. 5, 1985

[54] PIERCED EAR CLEANING AND STERILIZING APPARATUS

[76] Inventor: Lisa M. Karos, 12911 Gilmore Ave., Los Angeles, Calif. 90066

[21] Appl. No.: 506,022

[22] Filed: Jun. 20, 1983

[51] Int. Cl.³ .................... A61M 7/00; A61B 19/00; A61B 17/00; B65D 85/00
[52] U.S. Cl. .................... 206/210; 206/370; 128/330; 15/210 R; 132/90
[58] Field of Search ............ 206/210, 205, 63.3, 206/63.5, 363, 370; 132/90; 128/330; 15/210 R

[56] References Cited

U.S. PATENT DOCUMENTS 4,034,770 7/1977 Trecker ..................... 206/63.5

4,041,946 8/1977 Barton .

Primary Examiner—William T. Dixson, Jr.
Attorney, Agent, or Firm—Poms, Smith, Lande & Rose

[57] ABSTRACT

An apparatus for cleaning and sterilizing ear lobe holes for pierced earrings utilizes a string of absorbent material having attached thereto a firm tip. Both the string and the tip are maintained in a sealed envelope adjacent a pad of absorbent material saturated with an antiseptic fluid in contact with the string to saturate the string with the fluid. When it is desired to clean and sterilize the ear lobe hole, the package is opened and the string and tip are run through the ear lobe hole. The string both cleans the ear lobe hole and imparts the sterilizing fluid to the hole.

12 Claims, 5 Drawing Figures

U.S. Patent  Feb. 5, 1985  4,497,402
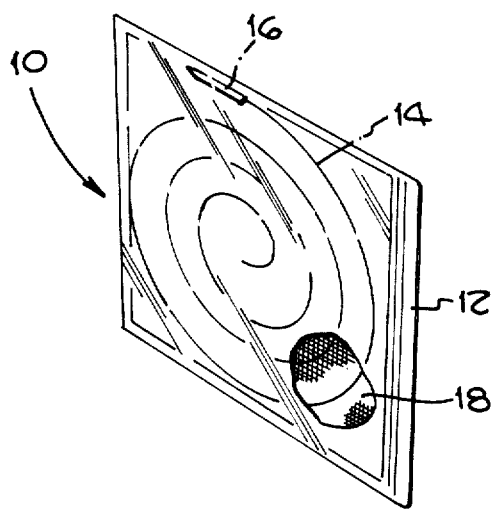
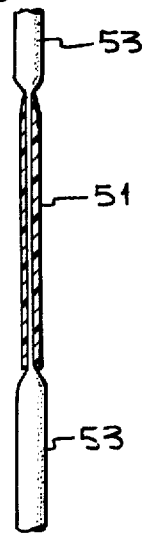
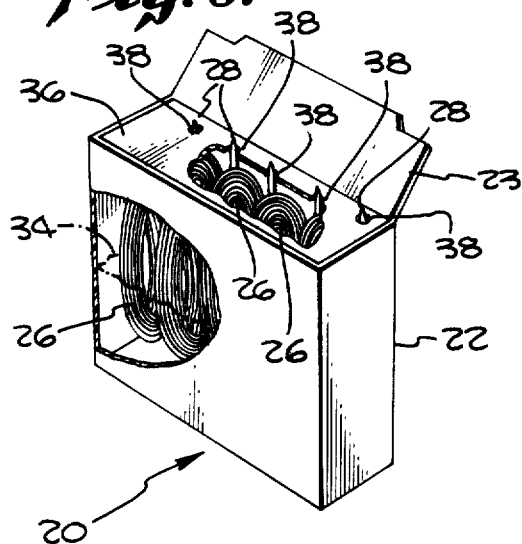
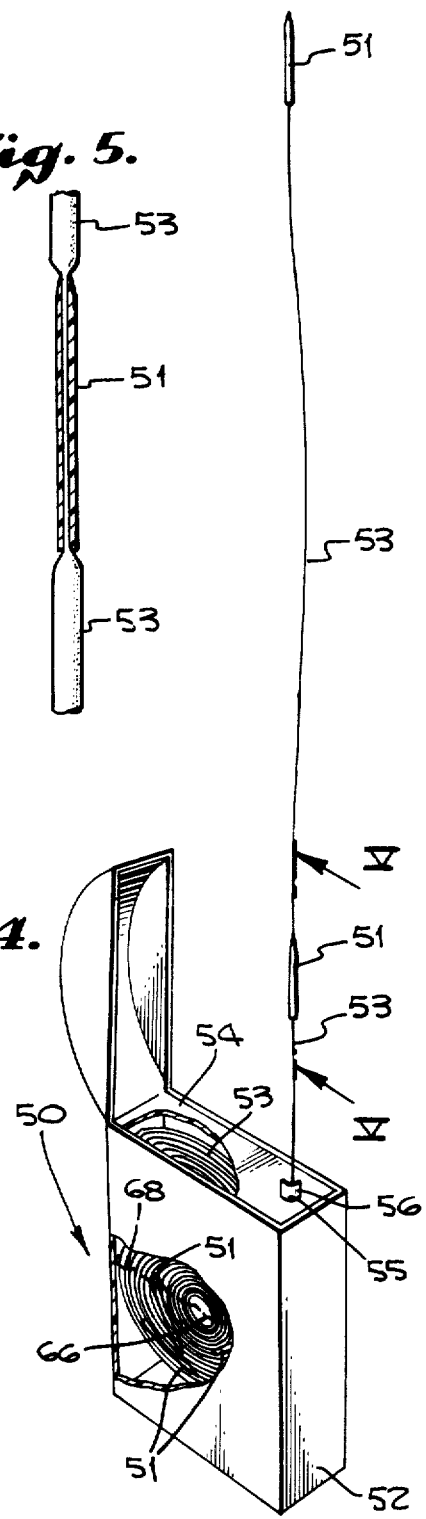

PIERCED EAR CLEANING AND STERILIZING APPARATUS

FIELD OF THE INVENTION

This invention relates generally to devices for cleaning the ear and, more particularly, to devices for cleaning and sterilizing the ear lobe after it has been pierced for a pierced earring.

BACKGROUND OF THE INVENTION

Pierced earrings are very popular items of jewelry. While many new devices have been invented to make the holes in the ear lobe for the earrings, no devices have been invented to aid in reducing the healing time for the ear after it has been pierced. Typically, it can take up to several months for the ear to properly heal after being pierced. During this time, a temporary "stud" is often worn in the ear and the ear is continually cleaned and sterilized with alcohol-saturated "cotton balls" or the like.

This cleaning and sterilizing procedure is far from satisfactory, as the alcohol aften does not penetrate the innermost portion of the hole in the ear, and only cleans the outer surface thereof. As a result, the healing process is delayed as the innermost portion of the pierced ear lobe is neither adequately cleaned nor sterilized and is thus the last portion to heal. If the hole could be easily cleaned and sterilized, the healing process could be greatly accelerated.

Additionally, even after the healing process has been completed and pierced earrings are worn on a regular basis, there is still a need to clean and sterilize the opening in the ear lobe. The only means currently of doing this is by the saturated cotton balls, cloths, or the like. As this method does not clean the central portion of the ear lobe hole, it is deficient.

Accordingly, it is the principal object of the present invention to accelerate the healing process for ears after they have been pierced for pierced earrings.

Yet another object of the present invention is to clean and sterilize the opening in the ear lobe for a pierced earring, both during and after the healing process.

SUMMARY OF THE INVENTION

The present invention, in a broad aspect, provides an apparatus for cleaning and sterilizing ear lobe holes for pierced earrings which includes an absorbent string, a firm tip disposed at the end of the string, a package for the string and the tip, and an antiseptic fluid disposed in the package in contact with the string. Prior to use, the string and the tip are disposed in the package with the string being saturated with the fluid. When cleaning and sterilizing of the ear lobe hole are desired, the string and the tip are removed from the packaging and run through the ear lobe hole. The string both cleans and imparts the antiseptic fluid to the ear lobe opening. The purpose of the tip is to guide the string through the ear lobe hole.

In one embodiment of the invention, the string and tip are contained in a single package adjacent a cotton pad saturated with antiseptic fluid in a moisture-proof package of foil or the like.

In another embodiment, a plurality of said strings and associated tips are packaged in a container filled with antiseptic fluid.

In yet another embodiment of the invention, a continuous string is wrapped around a roll placed in an openable container filled with antiseptic fluid. The string is selectively weakened at certain locations to allow the string to be broken into individual segments. The string is provided with rigid areas adjacent each of the weakened areas so that a continuous plurality of strings and associated tips are provided.

Other objects, features, and advantages of the present invention will become apparent from a consideration of the following detailed description and the accompanying drawings.

BRIEF DESCRIPTION OF THE DRAWINGS

FIG. 1 shows a perspective view of a first embodiment of a pierced ear cleaning and sterilizing apparatus according to the present invention;

FIG. 2 shows a detail view, partially in cross section, of a portion of the apparatus shown in FIG. 1;

FIG. 3 shows a perspective view of a second embodiment of a pierced ear cleaning and sterilizing apparatus according to the present invention;

FIG. 4 shows a third embodiment of a pierced ear cleaning and sterilizing apparatus according to the present invention; and FIG. 5 shows a cross-section view of the apparatus shown in FIG. 4, taken across the line V—V.

DETAILED DESCRIPTION

Referring more particularly to the drawings, FIG. 1 shows a perspective view of a pierced ear cleaning and sterilizing apparatus 10 according to the present invention. The apparatus 10 includes a length of string 14 of an absorbent material, such as cotton or nylon. Attached to the end of the string 14 is a firm tip 16 which may be of a hard fibrous or plastic material. The tip 16 may either be a separate element attached to the string 14 or may be a section of the string 14 which has been made to be firm, such as by the application of a liquid material which thereafter hardens. Preferably, the string 14 is approximately six inches in length and the tip 16 is approximately one inch in length. The tip 16 is also smaller in cross section than the string 14 and the cross section is approximately the same as that of a needle. Lastly, the string 14 and tip 16 are designed for one-time use only.

The string 14 and the tip 16 are packaged in an envelope 12 of a moisture-proof material such as foil or plastic. Disposed in the package 12 adjacent the string is a pad 18 of absorbent material which is impregnated with an antiseptic fluid. The fluid may be any common antiseptic fluid, such as alcohol, boric acid, or iodine. The pad 18 is disposed in the package 12 in contact with the string 14 so as to saturate the string 14 with the fluid.

When cleaning of the pierced ear lobe hole is desired, the package 12 is opened and the string 14 and accompanying tip 16 are removed. The tip 16 is pushed through the ear lobe hole and thereafter used to pull the length of the string 14 through the hole. The string 14 both cleans the ear lobe hole opening and imparts the antiseptic fluid with which it is saturated to the ear lobe hole. In this manner, the ear lobe hole is both cleaned and sterilized. When the apparatus 10 is used during the healing process after the ear has been pierced, the cleaning and sterilizing of the ear lobe hole will accelerate the healing process. Use of the apparatus 10 on the ear lobe after the healing process has been completed will also maintain the ear lobe hole in a clean and sterile condition.

FIG. 2 shows a detail cross-sectional view of an arrangement between the absorbent string 14 and the firm tip 16 whereby the tip 16 is a separate element affixed to the string 14.

FIG. 3 shows the second embodimemt of an apparatus 20 for cleaning and sterilizing ear lobe holes. In this embodiment 20, a plurality of strings 26 and tips 28 are packaged in a container 22 having an openable lid 23. Beneath the lid 23 is a panel 36 having a series of holes 38 through which the strings and tips are pulled. In FIG. 3, five such holes 38 are shown corresponding to the five separate strings 26 and accompanying tips 28 disposed in the container 22. While five tips and strings have been shown, a greater or lesser number could be used within the scope of the invention. The strings 26 and tips 28 shown in FIG. 3 are substantially identical to the strings 14 and tips 16 shown in FIG. 1.

Located within the container 22 is an antiseptic fluid 34 in contact with the absorbent strings 26. In this manner, the strings 26 are all saturated with the antiseptic fluid 34 prior to use.

Use of the embodiment of the invention 20 shown in FIG. 3 is very similar to that of the embodiment 10 shown in FIG. 1. When cleaning and sterilizing of the ear lobe hole is desired, one of the tips 28 is pulled out of the panel 36 which removes the tip and the string 26 from the container and the use of the string and tip is done in the manner previously described.

FIG. 4 shows a third embodiment 50 of an ear lobe cleaning and sterilizing apparatus according to the present invention. In this embodiment of the invention, a continuous string 53 with a plurality of tips 51 positioned thereon is wound about a roller 66 in a container 52 again containing an antiseptic fluid 68. As with the other embodiments, the antiseptic fluid 68 saturates the continuous string while it is still on the roller 66 and thereby insures that each of the string segments 58 and 62 are properly saturated.

The container 52 has an openable lid 70. Beneath the lid 70 is a panel 54 having a hole 55 through which the strings and tips are pulled. Adjacent the hole 55 is a gripping device 56 which is used to grip the continuous string. The gripping device maybe similar to those found on dental floss dispensers.

The continuous string wound 53 about the roller 66 is made of an absorbent material as was the case for the string 14 of the first embodiment. The tips 51 on the string 53 may be separate elements threaded on the string or may be areas of the string coated with a rigid material. The continuous string is weakened in the areas adjacent the tips 51. When it is desired to clean and sterilize the ear lobe, the continuous string is pulled through the hole 55 of the container 52 until one of the tips is immediately adjacent the gripping device 56. The string is then pulled until a new segment is broken off and thereafter used. In this manner, the continuous string is formed into a series of separate strings with corresponding tips for use.

Use of the separated string segments with this embodiment 50 of the invention is done in an identical manner with the separate string 14 and tip 16 for the first embodiment 10.

In the foregoing description of the present invention, several embodiments of the invention have been disclosed. It is to be understood that other mechanical and design variations are within the scope of the present invention. Thus, by way of example and not of limitation, the foil packaging described for the first embodiment could be replaced with a plastic "bubble" packaging. Accordingly, the invention is not limited to the particular arrangements which have been illustrated and described in detail herein.

What is claimed is:

1. In an apparatus for cleaning and sterilizing ear lobe holes for pierced earrings, including a packaging means, an improved disposable apparatus, comprising:
    absorbent string means;
    firm tip means disposed at one end of said string means; and
    antiseptic fluid means, disposed in said packaging means in contact with said string means, whereby said string means and said tip means are packaged in said packaging means, with said string means being saturated with said fluid, until cleaning and sterilizing of said ear lobe is desired, whereupon said string means and said tip means are removed from said packaging means and run through said ear lobe hole, said string means both cleaning said ear lobe hole and imparting said antiseptic fluid to said hole.

2. An apparatus as defined in claim 1, wherein said string means comprises a single length of absorbent cotton material.

3. An apparatus as defined in claim 1, wherein said string means comprises a single length of absorbent nylon material.

4. An apparatus as defined in claim 1, wherein said string means comprises a plurality of strings of absorbant cotton material, with each of said strings having said tip means at the end thereof.

5. An apparatus as defined in claim 1, wherein said tip means comprises a hard fibrous material.

6. An apparatus as defined in claim 1, wherein said tip means comprises a plastic material.

7. An apparatus as defined in claim 1, wherein said fluid means comprises alcohol.

8. An apparatus as defined in claim 1, wherein said fluid means comprises boric acid.

9. An apparatus as defined in claim 1, wherein said fluid means comprises iodine.

10. An apparatus as defined in claim 1, wherein said packaging means comprises rigid container means having an openable top.

11. An apparatus as defined in claim 1, wherein:
    said string means comprises a continuous string of absorbent cotton adapted to break into a plurality of separate string segments; and
    said tip means comprises a plurality of fibrous elements formed on said string adjacent the portions of said string adapted to break into said segments, whereby said plurality of string segments each contain a fibrous element.

12. In an apparatus for cleaning and sterilizing ear lobe holes for pierced earrings, including an envelope packaging means, an improved disposable apparatus, comprising:
    at least one string of absorbent material;
    a firm tip disposed at the end of said string; and,
    a pad of absorbent material saturated with an antiseptic fluid disposed in said envelope in contact with said string to saturate said string with said fluid, wherby said string and tip are removed from said package and run through said ear lobe hole to clean and sterilize said hold.

* * * * *